US009072546B2

(12) United States Patent
Trieu et al.

(10) Patent No.: US 9,072,546 B2
(45) Date of Patent: Jul. 7, 2015

(54) SPINAL CONSTRUCTS WITH IMPROVED LOAD-SHARING

(75) Inventors: Hai H. Trieu, Cordova, TN (US); Jon A. Harmon, Byhalia, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 664 days.

(21) Appl. No.: 12/869,245

(22) Filed: Aug. 26, 2010

(65) Prior Publication Data

US 2012/0053635 A1 Mar. 1, 2012

(51) Int. Cl.
*A61B 17/70* (2006.01)
(52) U.S. Cl.
CPC ......... *A61B 17/7032* (2013.01); *A61B 17/7004* (2013.01); *A61B 17/7011* (2013.01); *A61B 17/7035* (2013.01); *A61B 17/7019* (2013.01); *A61B 17/7026* (2013.01); *A61B 17/7031* (2013.01)

(58) Field of Classification Search
CPC .......... A61B 17/7026; A61B 17/7031; A61B 17/7032; A61B 17/7035; A61B 17/7038
USPC .................. 606/254–259, 265–274
See application file for complete search history.

(56) References Cited

U.S. PATENT DOCUMENTS

| 5,415,661 | A | 5/1995 | Holmes |
| 6,267,764 | B1 | 7/2001 | Elberg |
| 2003/0191470 | A1 | 10/2003 | Ritland |
| 2005/0143737 | A1 | 6/2005 | Pafford et al. |
| 2005/0143823 | A1 | 6/2005 | Boyd et al. |
| 2007/0191832 | A1* | 8/2007 | Trieu .............................. 606/61 |
| 2007/0233066 | A1* | 10/2007 | Rezach .......................... 606/61 |
| 2008/0071273 | A1 | 3/2008 | Hawkes et al. |
| 2008/0161853 | A1 | 7/2008 | Arnold et al. |
| 2008/0306517 | A1* | 12/2008 | Cain et al. ..................... 606/246 |
| 2009/0062868 | A1* | 3/2009 | Casutt .......................... 606/316 |
| 2009/0182380 | A1 | 7/2009 | Abdelgany |
| 2009/0264937 | A1 | 10/2009 | Parrott |
| 2010/0030267 | A1* | 2/2010 | Winslow et al. ............... 606/246 |
| 2010/0030279 | A1 | 2/2010 | Flynn et al. |
| 2010/0042157 | A1 | 2/2010 | Trieu |
| 2010/0057140 | A1 | 3/2010 | Zucherman et al. |
| 2010/0100137 | A1 | 4/2010 | Justis et al. |
| 2010/0168795 | A1 | 7/2010 | Winslow et al. |
| 2011/0257687 | A1* | 10/2011 | Trieu et al. .................... 606/267 |

OTHER PUBLICATIONS

U.S. Appl. No. 12/762,421, filed Apr. 19, 2010, titled "Load Sharing Bone Fastener and Methods of Use".
U.S. Appl. No. 12/394,362, filed Feb. 27, 2009, titled "Vertebral Rod System and Method of Use".

* cited by examiner

*Primary Examiner* — Jerry Cumberledge
*Assistant Examiner* — Nicholas Plionis

(57) ABSTRACT

A spinal construct for implantation in a patient to provide stabilization to spinal structure with improved load sharing includes a flexible spinal rod having a first end and a second end, the spinal rod being configured to provide stabilization to spinal structure. It also includes a first bone fastener configured to securely attach to the flexible spinal rod and a second bone fastener configured to securely attach to the flexible spinal rod. The second bone fastener is a dynamic fastener arranged to provide motion in one direction more than another direction. The flexible spinal rod and the second bone fastener are oriented to cooperate in a manner that achieves load sharing by dynamically flexing under applied loads in a manner that distributes stresses and strains between the flexible spinal rod and the second bone fastener.

20 Claims, 9 Drawing Sheets

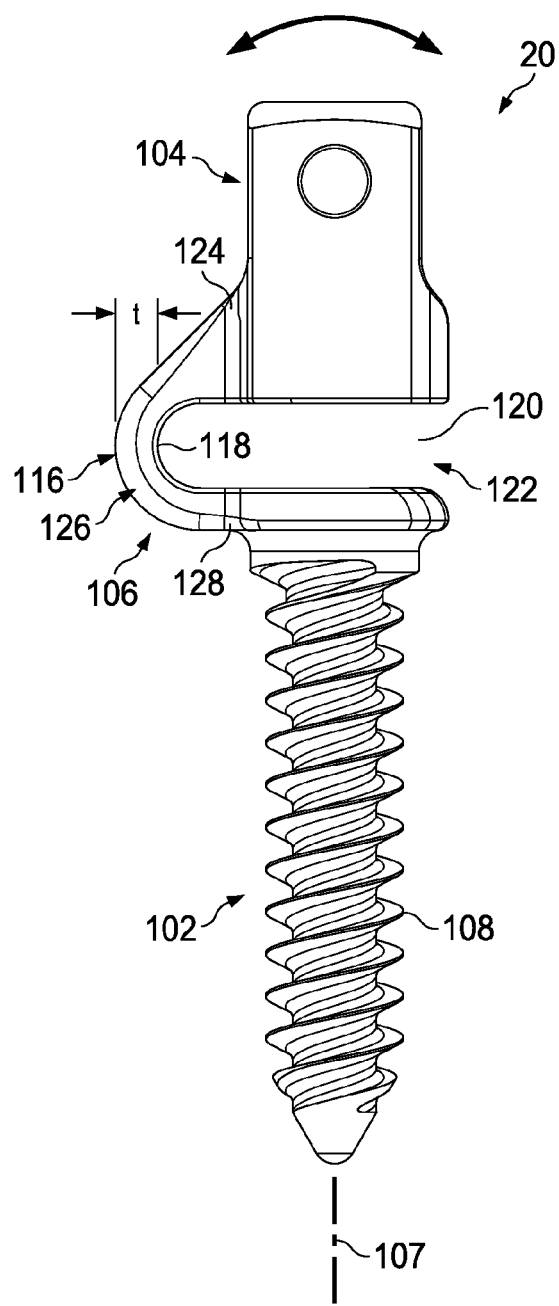
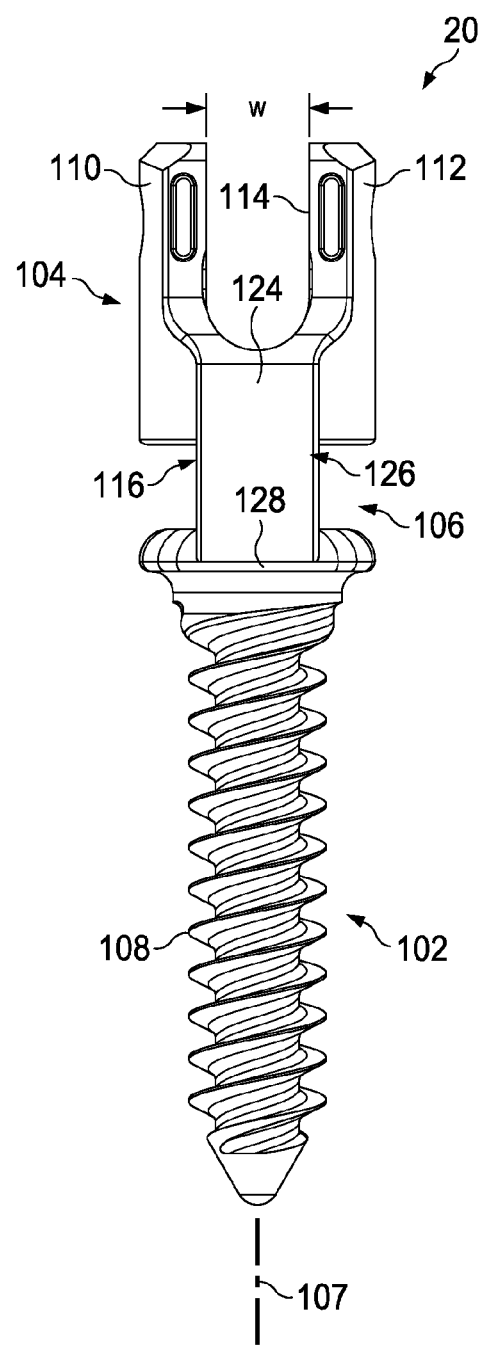
Fig. 2
Fig. 3

SPINAL CONSTRUCTS WITH IMPROVED LOAD-SHARING

FIELD OF THE INVENTION

The present disclosure is directed to stabilization constructs, and more particularly, to stabilization constructs with improved load sharing.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders include discectomy, laminectomy, fusion and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods may be attached via fasteners to the exterior of two or more vertebral members.

Conventional stabilization constructs can be improved to reduce stress carried by I individual bone structures and implanted components.

The fasteners and systems disclosed herein overcome one or more of the shortcomings of prior art devices.

SUMMARY

In one exemplary aspect the present disclosure is directed to a spinal construct for implantation in a patient to provide stabilization to spinal structure with improved load sharing. The construct includes a flexible spinal rod having a first end and a second end, the spinal rod being configured to provide stabilization to spinal structure. It also includes a first bone fastener configured to securely attach to the flexible spinal rod and a second bone fastener configured to securely attach to the flexible spinal rod. The second bone fastener is a dynamic fastener arranged to provide motion in one direction more than another direction. The flexible spinal rod and the second bone fastener are oriented to cooperate in a manner that achieves load sharing by dynamically flexing under applied loads in a manner that distributes stresses and strains between the flexible spinal rod and the second bone fastener.

In some aspects, the first bone fastener comprises a dynamic fastener arranged to provide motion in one direction more than another direction. The flexible spinal rod, the first bone fastener, and the second bone fastener are oriented to cooperate in a manner that achieves load sharing by dynamically flexing under applied loads in a manner that distributes stresses and strains between the flexible spinal rod and both the first and the second bone fasteners.

In some aspects, the second bone fastener comprises a flexible bumper configured to dampen movement in at least one of flexion and extension.

In another exemplary aspect, the present disclosure is directed to a spinal construct for implantation in a patient to provide stabilization to spinal structure with improved load sharing. The construct includes a flexible spinal rod having a first end and a second end, and being configured to provide stabilization to spinal structure. The spinal rod is configured in a manner that provides relatively more motion in a flexion and extension direction and relatively less motion in a lateral direction. The construct also includes a first bone fastener configured to securely attach to the flexible spinal rod. The first bone fastener being configured in a manner that provides relatively more motion in a flexion and extension direction and relatively less motion in a lateral direction. The flexible spinal rod and the first bone fastener are oriented to cooperate in a manner that achieves load sharing by dynamically flexing under applied loads in a manner that distributes stresses and strains between the flexible spinal rod and the first bone fastener.

Further aspects, forms, embodiments, objects, features, benefits, and advantages of the present invention shall become apparent from the detailed drawings and descriptions provided herein.

BRIEF DESCRIPTION OF THE DRAWINGS

The accompanying drawings serve to exemplify some of the embodiments of this invention.

FIGS. 2 and 3 are illustrations of an exemplary dynamic bone fastener for securing an dynamic spinal rod in accordance with one or more aspects of the present disclosure.

DETAILED DESCRIPTION

Figure 1:
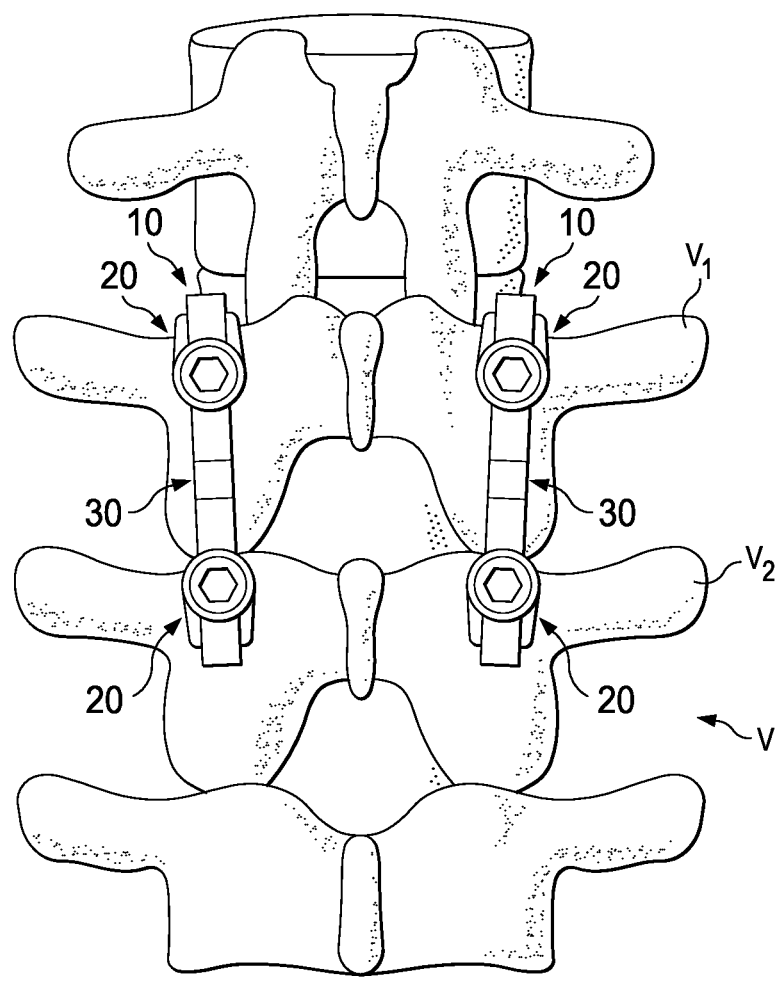
FIG. 1 is an illustration of a portion of an exemplary vertebral column having exemplary spinal constructs attached thereto in accordance with one or more aspects of the present disclosure.

The present disclosure relates generally to the field of implantable bone stabilization constructs, and more particularly to constructs having at least one dynamic bone fastener and a dynamic rod that cooperate together to achieve load sharing while providing stabilizing support to bone structure and tissue. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

The exemplary embodiments of the bone stabilization constructs are configured to provide stabilization to patient tissue, while at the same time distributing stresses and loads carried by the individual bone fastener and rod components. Distributed stresses result in increased resistance to wear and reduced stress and strain while maintaining or increasing the range of motion of conventional constructs. In addition, some embodiments are configured to provide increased directional motion in some directions, through particular fastener or rod designs, while maintaining or stabilizing directional motion in other directions. In some examples, in order to achieve a maximized directional motion, the bone fasteners and the rod work in concert to provide both maximized motion in some directions and more stabilized support in the other directions.

The constructs and construct components in the present disclosure may be employed to treat spinal disorders such as, for example, degenerative disc disease, disc herniation, osteoporosis, spondylolisthesis, stenosis, scoliosis and other curvature abnormalities, kyphosis, tumors, and fractures, among other disorders. These constructs and construct components may be utilized using surgical treatments or techniques including open surgery and minimally invasive procedures, and may be used to treat, for example, discectomy, laminectomy, fusion, bone graft, implantable prosthetics and/or dynamic stabilization applications. It is contemplated that the present disclosure may be employed with other osteal and bone related applications, including those associated with diagnostics and therapeutics. It is further contemplated that the disclosed constructs may be employed in a surgical treatment with a patient in a prone or supine position, employing a posterior, lateral or anterior approach. The present disclosure may be employed with procedures for treating the lumbar, cervical, thoracic and pelvic regions of a spinal column.

FIG. 1 shows exemplary spinal rod constructs 10 in place on a portion of a vertebral column V. Each exemplary construct 10 in FIG. 1 includes two bone fasteners 20 connected by a longitudinally extending spinal rod 30. In each construct 10, a first bone fastener 20 is anchored to a first vertebra V1 and a second bone fastener 20 is anchored to a second vertebra V2. The spinal rod 30 connects the fasteners to each other, providing stability to the vertebrae. As will be described below, the bone fasteners 20 are dynamic fasteners and the spinal rod 30 is a dynamic rod. As such, they each include at least one deformable or flexible section along the bone fastener 20 and at least one deformable section along the spinal rod 30. Upon fixation of the spinal rod construct with vertebrae V, the bone fasteners 20 and spinal rod 30 each are configured to provide changing or a fixed level of resistance to movement during flexion, extension and/or torsion of the spine. Such constructs allow the overall strain and stress to be distributed between the rod and the fasteners in order to increase the level of load sharing, the dynamic behavior and/or the overall range of motion (ROM) of the construct while maintaining durability of the spinal implants and the bone-screw interface.

FIGS. 2 and 3 show one example of a bone fastener 20 suitable for use in the constructs 10 in FIG. 1. The bone fastener 20 includes a fixation portion 102, a connection portion 104, and a flexible portion 106. The fastener 100 includes a longitudinal axis 107, shown for reference. The fixation portion 102 is configured to interface or engage with bone structure, such as the vertebrae V1, V2 to secure the bone fastener 20 in place. In the embodiment shown, the fastener 20 is a bone screw and the fixation portion 102 comprises outwardly extending threads 108 configured to penetrate boney tissue. However, in other embodiments, the fixation portion is a hook, clamp, or other structure configured to interface or engage the bone structure.

The connection portion 104 is configured to engage the spinal rod 30 shown in FIG. 1. In this embodiment, the connection portion 104 is a U-shaped receiver comprising a first arm 110 and a second arm 112, spaced to receive the spinal rod 30. The receiver includes a threaded inner surface 114 configured to threadably receive a set screw to secure the spinal rod in place in the receiver. Although shown as a U-shaped receiver, other embodiments of the connection portion 104 include bores or through holes, clamps, and other constructs and arrangements for receiving a spinal rod.

The flexible portion 106 enables dynamic movement between the fixation portion 102 and the connection portion 104, as indicated by the directional arrows in FIG. 2. It is configured to allow the connection portion 104 to pivot within a preestablished range at least in both a rearward and forward direction. It provides stability and structural integrity while reducing stress on spinal elements, the bone tissue engaged with the fixation portion 102, the supporting structure 104, and a spinal rod attached thereto. Here, the flexible portion 106 includes an arcuate C-shaped connecting portion 116 extending between and connecting the fixation portion 102 and the connection portion 104. It is contemplated that the connecting portion 116 may have alternative configurations, such as U-shaped, V-shaped, or W-shaped, for example. The connecting portion 116 is disposed between the fixation portion 102 and the connection portion 104 such that connecting portion 104 is longitudinally aligned with the fixation portion 102 along longitudinal axis 107. The connecting portion 116 includes an inner surface 118 that defines a cavity 120 and an open end 122 such that the connecting portion 116 is configured to provide dampening. Here, the connecting portion 116 flexes as a result of elastic deformation. In this embodiment, because the connecting portion 116 is disposed to one side of the fastener 100, the flexible portion 106 is arranged to flex about a point offset from the longitudinal axis 107 of the fastener 20. Because the center of rotation is offset, the dynamic fastener provides a non-symmetrical rotational movement that may be desirable to treat spinal conditions. It is contemplated that the components of the bone fastener 20 may be monolithically formed, integrally connected or arranged with attaching elements.

Because of its elastic nature, the connecting portion 116 provides biasing resistance to movement of the connecting portion 104 and the anchoring portion 102. The connecting portion 116 has a first end 124, a flexible joint portion 126, and a second end 128. The first end 124 and the second end 128 are flexible relative to a mid-point of the flexible joint portion 126. The connecting portion 104 is connected with first end 124 and the anchor portion 102 is connected with second end 128. It is contemplated that the connecting portion 116 may be structurally arranged to provide increasing, variable, constant and/or decreasing resistance.

It is contemplated that the anchoring portion 102, the connecting portion 104, and the flexible portion 106 may be variously dimensioned, for example, with regard to length, width, diameter and thickness. It is further contemplated that the respective cross-sectional geometry or area of portions 102, 104, 106 may have various configurations, for example, round, oval, rectangular, irregular, consistent, variable, uniform and non-uniform.

The connecting portion 116 may have a variable thickness t according to the requirements of the particular application. It is envisioned that thickness t of the connecting portion 116 may be in a range of 0.5 millimeters (mm) to 6.0 mm, and preferably 1.0 mm to 4.0 mm. The connecting portion 116 also has a width w. It is contemplated that the width w may be in a range 1 mm to 12 mm, and preferably 3 mm to 8 mm. In one embodiment, the connecting portion 116 is enlarged relative to anchoring portion 102 and the connecting portion 104 such that width w spans a greater distance than the profile of portions 102, 104.

Some embodiments of the connecting portion 116 have a wide, narrow, round, or irregular configuration. The connecting portion 116 can be variously configured and dimensioned with regard to size, shape, geometry and material. The connecting portion 116 may also have one or a plurality of elements connecting anchoring portion 102 and the connecting portion 104 such as spaced apart portions, staggered patterns and mesh. The connecting portion 116 may be fabricated from the same or alternative material to anchoring portion 102 and the connecting portion 104. It may also have a different cross-sectional area, geometry or material property such as strength, modulus and flexibility relative to anchoring portion 102 and the connecting portion 104. The connecting portion 116 may be connected to the anchoring portion 102 and the connecting portion 104 using various methods and structure including molding of a continuous component, mechanical fastening, adhesive bonding and combinations thereof.

It is envisioned that the connecting portion 116 operates as a flexible hinge, which can be offset forward or backward relative to the axis 107 of the bone fastener 20 to modify the flexibility or stiffness of the spinal rod construct 10. It is further envisioned that particular parameters of the bone fastener 20 may be selected to modulate the flexibility or stiffness of the spinal rod construct including the material modulus that may correlate to the hardness of a resistance member discussed below. For example, parameters may be selected to include a porosity level in a range of 1% to 75%, and preferably 5% to 50%, which may include a void volume in a range of 1% to 75%, and preferably 5% to 50%. These parameters allow modification of the properties or performance of bone fastener 20 such as strength, durability, flexibility (or stiffness), overall profile and the ability to employ a percutaneous approach, for a particular application.

During movement of vertebrae V, for example, in flexion, extension and/or torsion, the connecting portion 104 moves relative to the anchor portion 102 to facilitate relative flexibility and/or movement of the rod 30 and/or other components of the spinal rod construct 10. The first end 124 and second end 128 can flexibly expand, compress and/or rotate in torsion relative to the joint portion 126 such that the connecting portion 116 expands and compresses the cavity 120. The open end 122 can also expand and compress. This configuration increases resistance during expansion, compression and/or rotation of the connecting portion 116. The increase of resistance during flexion, extension and/or torsion provides limited movement of vertebrae V for load sharing and/or dynamic stabilization of the treated area of the spine.

Because of the orientation of the connecting portion 116, having a greater width w than thickness t, the bone fastener 20 is configured in a manner to provide directional movement, permitting more motion in the flexion and extension direction, and permitting less motion in the lateral directions. In some embodiments, the connecting portion 116 is designed to permit motion substantially only along a single plane. In such embodiments, due to the structural configuration, this planar motion is permitted substantially in the flexion and extension plane, aligned to extend through the longitudinal axis of the spinal rod 30.

Figure 4:
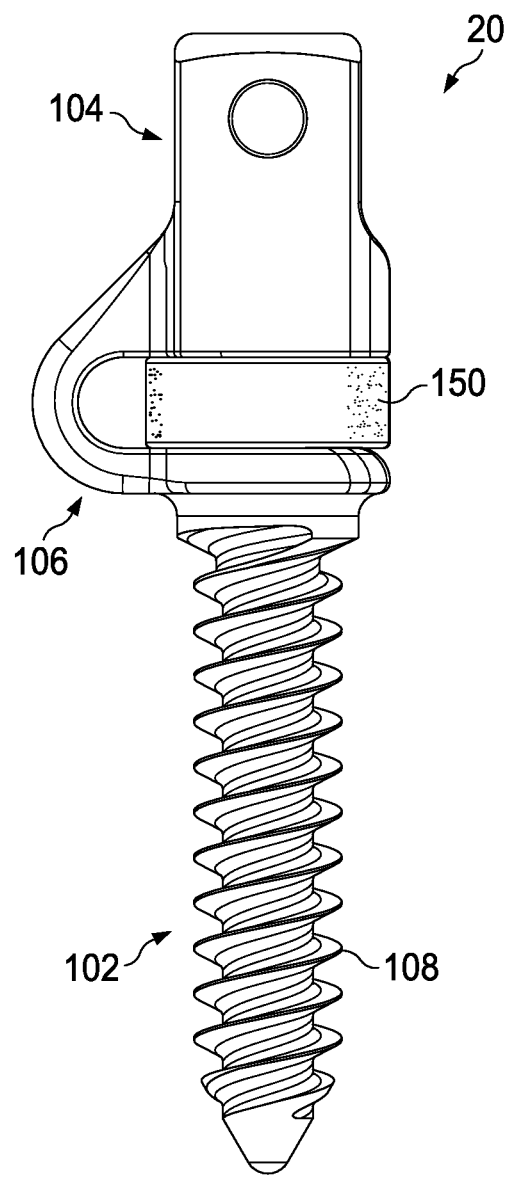
FIG. 4 is an illustration of an exemplary dynamic bone fastener for securing an dynamic spinal rod having a bumper member in accordance with one or more aspects of the present disclosure.

In one embodiment, the cavity 120 is configured for disposal of a resistance member, such as, for example, a bumper 150, as shown in FIG. 4. It is envisioned that the bumper 150 may be monolithically formed, integrally connected, employ fastening elements and/or adhesives for disposal within the flexible portion 106.

The bumper 150 is elastic and configured to provide variable resistance to movement of portions 102, 104, and 106. It is contemplated that the bumper 150 can provide increasing, variable, constant and/or decreasing resistance. The bumper 150 is disposed within the cavity 120 and in some embodiments, engages the surface 118 in a close fitting engagement. The bumper 150 can be variously configured with regard to size, shape, for example, round, oblong, rectangular, triangular, spherical, and irregular shapes. It is envisioned that the bumper 150 has a hardness in the range of 30 Shore A to 55 Shore D. The material of the bumper 150 can be solid or porous, homogeneous or heterogeneous, single polymer or a blend/composite of more than one polymer. It is contemplated that the resiliency of the bumper 150 can prevent creep and improve shape recovery of the spinal rod construct. It is envisioned that the bumper 150 is configured to prevent and/or resist closing of the open end 122. It is further envisioned that bumper 150 is secured in place with the connecting portion 116, and desirably mechanically secured therewith in a configuration to present migration and expulsion therefrom. In other embodiments, the bumper 150 can be textured, encapsulated, adhesively bonded and/or over molded with bone fastener 20. The bumper 150 can be inserted within the cavity 120 for assembly, or formed in situ by, for example, a pouch, bag or balloon with the bumper configuration being inserted into cavity 120 and injected with a curable manner.

Although the exemplary fasteners shown are mono-axial fasteners, in other embodiments, the fasteners are multi-axial type bone fasteners that include additional articulation, such as a ball and socket joint, between the fixation portion 102 and the connection portion 104. Some examples of bone fasteners, including multi-axial type fasteners that may be used in the constructs described herein are found in U.S. patent application Ser. No. 12/762,421, filed Apr. 19, 2010, titled Load Sharing Bone Fastener and Methods of Use, incorporated herein by reference.

Figure 5:
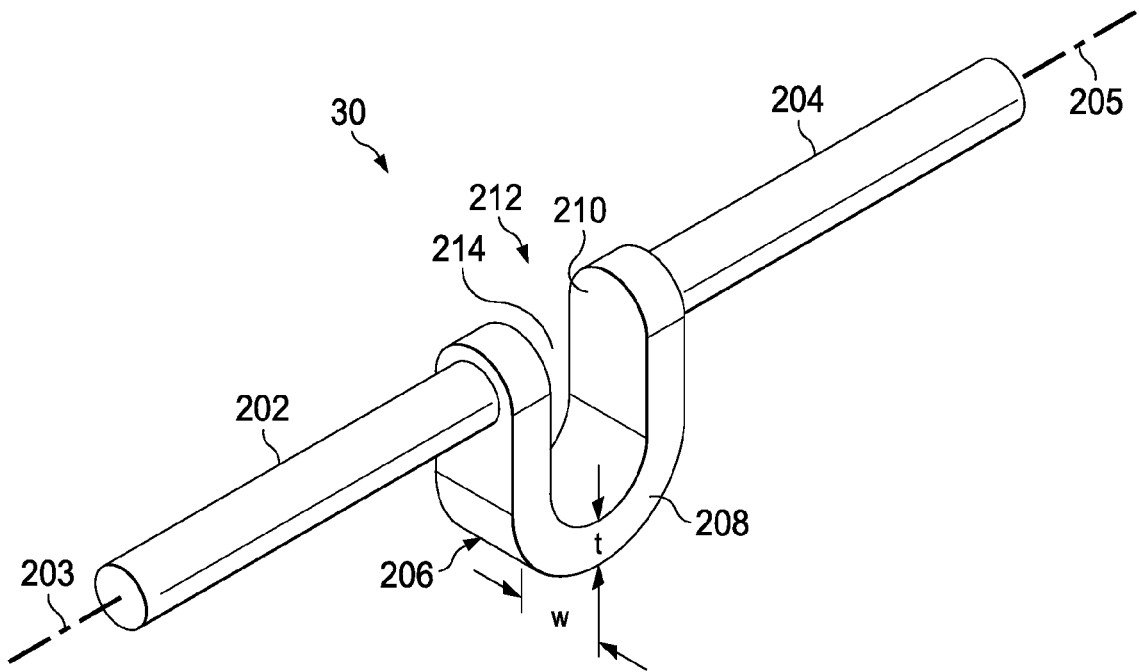
FIG. 5 is an illustration of an exemplary dynamic spinal rod for securing to a dynamic fastener in accordance with one or more aspects of the present disclosure.

The spinal rod construct 10 in FIG. 1 includes the spinal rod 30. An exemplary spinal rod 30 is described with reference to FIG. 5. The spinal rod 30 includes a first elongated section 202 that defines a first longitudinal axis 203 and a second elongated section 204 that defines a longitudinal axis 205. It also includes an intermediate section 206 connected with sections 202, 204, and disposed therebetween. The components of the spinal rod 30 may be monolithically formed, integrally connected, or arranged with attaching elements. Here, the intermediate section 206 is flexible relative to sections 202, 204, and is configured to provide resistance to movement of sections 202, 204. Depending on the embodiment, the intermediate section 206 may provide increasing, variable, constant, and/or decreasing resistance. It is contemplated that sections 202, 204, 206 can be variously dimensioned, for example, with regard to length, width, diameter and thickness. It is further contemplated that the respective cross-section of sections 202, 204, 206 may have various configurations, for example, round, oval, rectangular, irregular, uniform and non-uniform. Section 202 may have a different cross-sectional area, geometry, material or material property such as strength, modulus or flexibility relative to section 204.

The intermediate section 206 may have a variable thickness t according to the requirements of the particular application. In some embodiments, the thickness t of intermediate section 206 may be in a range of 1-10 mm, preferably in a range of 2-8 mm, and most preferably in a range of 3-5 mm. It is further envisioned that the cross-sectional geometry or area of intermediate section 206 can be uniform, non-uniform, consistent or variable. It may also have a width w, with the width w being greater than the thickness t.

The intermediate section 206 may be configured as a flexible joint having a wide, narrow, round or irregular configuration. It is further envisioned that intermediate section 206 can be variously configured and dimensioned with regard to size, shape, thickness, geometry and material. The intermediate section 206 may also have one or a plurality of elements connecting sections 202, 204 such as spaced apart portions, staggered patterns, and mesh. It may be fabricated from the same or alternative material to sections 202, 204. It may have a different cross-sectional area, geometry or material property such as strength, modulus and flexibility relative to sections 202, 204. The intermediate section 206 may be connected to sections 202, 204 using various methods and structure including molding of a continuous component, mechanical fastening, adhesive bonding and combinations thereof. The intermediate section 206 may be a flexible hinge configuration, which can be offset forward or backward relative to a central axis of the rod 30 to modify the flexibility or stiffness of the spinal rod construct 10. It is further envisioned that particular parameters may be selected to modulate the flexibility or stiffness of the spinal rod construct including the cross-sectional area (or thickness) of intermediate section 206, material modulus that may correlate to the hardness of bumper 250 discussed below, modification of porosity in a range of 0-30 percent which may include modification of void volume in a range of 10 microns-1 mm, as well as rod material properties. These parameters allow modification of the properties or performance of the spinal rod construct such as strength, durability, flexibility (or stiffness), overall profile and the ability to employ a percutaneous approach, for a particular application.

The intermediate section 206 includes a flexible joint member 208, which has a C-shaped configuration and defines a corresponding shaped arcuate inner surface 210 and an open end 212. It is contemplated that joint member 208 may have alternative configurations such as U-shaped, V-shaped or W-shaped. It is further contemplated that the spinal rod 30 may include one or a plurality of intermediate sections 206 spaced along the length of rod 30, as discussed below. In embodiments including a plurality of sections 206, the multiple sections 206 may be disposed in similar, or alternative orientations such as aligned, non-aligned, offset, open end facing or not facing vertebrae and alternate angular orientation.

In this embodiment, because the joint member 208 is disposed to one side of the first and second rod sections 202, 204, the joint member 208 is arranged to flex about a point offset from the longitudinal axes 203, 205 of the spinal rod 30. Because the center of rotation is offset, the dynamic rod provides a non-symmetrical rotational movement that may be desirable to treat spinal conditions.

Figure 6:
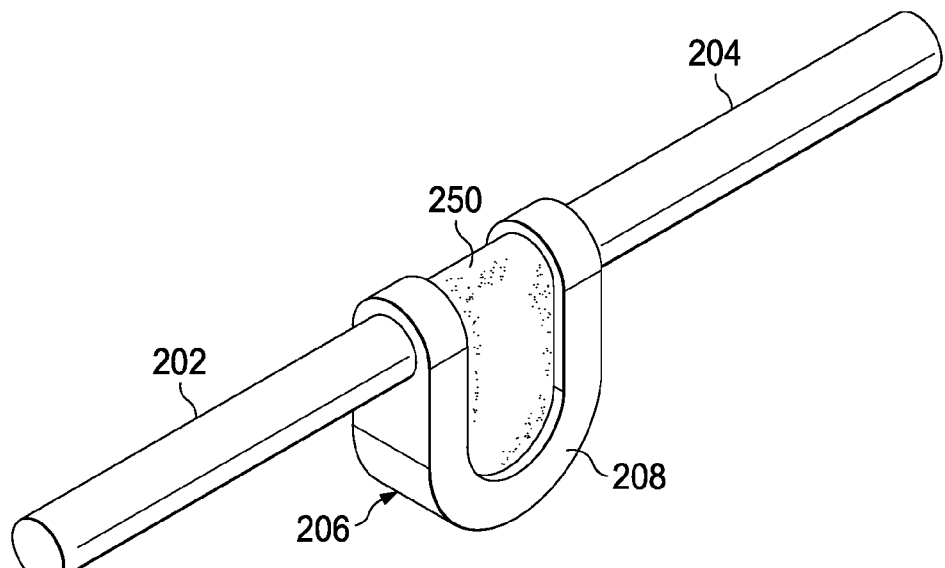
FIG. 6 is an illustration of an exemplary dynamic spinal rod having a bumper for securing to a dynamic fastener in accordance with one or more aspects of the present disclosure.

The inner surface 210 defines a cavity 214. The cavity 214 is configured to receive and house a resistance member, such as, for example, a bumper 250, as shown in FIG. 6. The bumper 250 is elastic and configured to provide variable resistance to movement of sections 202, 204 and 206. It is contemplated that the bumper 250 can provide increasing, variable, constant and/or decreasing resistance. The bumper 250 is disposed within cavity 214 and engages the surface 210 in a close fitting engagement. The bumper 250 can be variously configured with regard to size, shape, for example, round, oblong, rectangular, triangular, spherical, and irregular shapes. It is envisioned that the bumper 250 has a hardness in the range of 20 Shore A to 55 Shore D, and preferably between 70 and 90 Shore A. The material of the bumper 250 can be solid or porous, homogeneous or heterogeneous, single polymer or a blend/composite of more than one polymer. It is contemplated that the resiliency of the bumper 250 can prevent creep and improve shape recovery of the spinal rod construct. It is envisioned that the bumper 250 is configured to prevent and/or resist closing of the open end 212. The bumper 250 can be inserted with cavity 214 for assembly, or formed in situ by, for example, a pouch, bag or balloon with the bumper configuration being inserted into cavity 214 and injected with a curable material.

During flexion and extension of the spinal rod 30, the first section 202 moves relative to the second section 204 from a first or neutral orientation to a second displaced orientation. In the first orientation, the first and second sections 202, 204 are disposed so that the longitudinal axis 203 is disposed at a first angle (including 0 degrees) relative to the longitudinal axis 205 about the flexible joint member 208. In the second orientation, the first and second sections 202, 204 are disposed so that the longitudinal axis 203 and the longitudinal axis 205 are at a second angle relative to the first (including 0 degrees). The bumper 250 engagingly interacts with the intermediate section 206 in a configuration that provides increasing resistance to movement of sections 202, 204 from the first orientation to the second orientation. Movement of the components of the spinal rod construct between one or a plurality of orientations is contemplated and may include a range of increasing and decreasing levels of resistance of the components of the spinal rod construct.

The first section 202 and second section 204 can flexibly expand, compress and/or rotate in torsion relative to the intermediate section 206 such that arm 36 expands and compresses cavity 40. The joint member 208 can flexibly expand circumferentially about bumper 250 such that the first section 202 and second section 204 compress the bumper 250; or the joint member 208 can flexibly compress circumferentially about the bumper 250. This configuration increases resistance during expansion and compression of the intermediate section 206. The increase of resistance during flexion, extension and/or torsion provides limited movement of vertebrae V for load sharing and/or dynamic stabilization of the treated area of the spine.

Because of the orientation of the joint member 208, having a greater width w than thickness t, the spinal rod 30 is configured in a manner to provide directional movement, permitting more motion along a plane that includes the flexible joint member 208, and permitting less motion in planar directions not along a plane including the flexible joint member 208. In some embodiments, the joint member 208 is designed to permit motion substantially only along a single plane.

In assembly, operation and use, the spinal construct 10 including bone fastener 20 and spinal rod 30 is employed with a surgical procedure for treatment of a spinal disorder affecting a section of a spine of a patient, as discussed herein.

Figure 7:
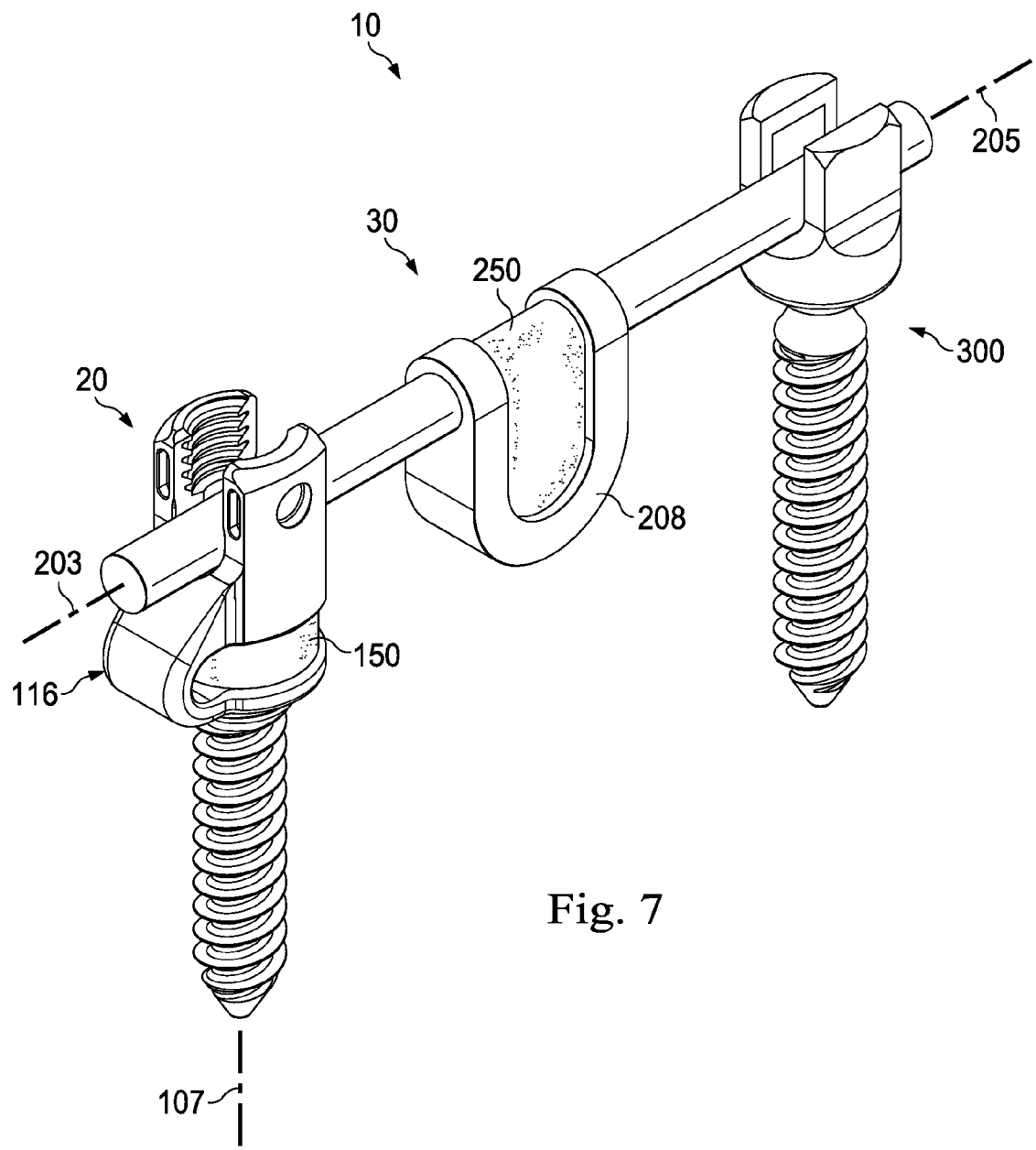
FIG. 7 is an illustration of an exemplary spinal construct including a single dynamic bone fastener and a dynamic spinal rod for single level spinal stabilization in accordance with one or more aspects of the present disclosure.

FIG. 7 shows one embodiment of an exemplary spinal rod construct 10 for treating a single level of a spinal structure. This embodiment includes a dynamic screw 20, the dynamic spinal rod 30, and a non-flexible conventional multi-axial screw 300. Accordingly, the spinal rod construct in FIG. 7 includes two cooperating dynamic structures that achieve load sharing by together absorbing loads resulting from flexion or extension. By distributing loads in both the dynamic screw 20 and the spinal rod 30, stress and strain carried by each of the components individually is reduced, resulting in increased durability. In addition, the combination of a flexible fastener and flexible rod result in an increased dynamic nature of the construct, providing greater dynamic properties. Some embodiments have improved range of motion (ROM) over constructs using only a dynamic rod or dynamic screw. Because each component carries less stress and strain than it would if used alone, the reliability of the bone-screw interface may be increased, potentially reducing failure at those interfaces. In addition, reducing the stress and strain carried by each component individually increases reliability and durability of the component themselves, including reducing midshaft screw fractures. It should be noted that the bumpers 150, 250 in the spinal construct 10 are optional and that the construct may be formed of any flexible devices, with or without bumpers.

In the embodiment shown, particular advantages are obtained due to the directional displacement achieved by the particular construct design. That is, as explained above, the bone fastener 20 is configured in a manner to provide directional movement, permitting more motion in the flexion and extension direction, and permitting less motion in the lateral directions. This is due to the nature and alignment of the flexible connecting portion 116. In some embodiments, the connecting portion 116 is designed to permit motion substantially only along a single plane. In such embodiments, due to the structural configuration, this planar motion is permitted only in the flexion and extension plane, aligned to extend through the longitudinal axis of the spinal rod 30.

In addition, the spinal rod 30 is also configured to provide a cooperating advantage by permitting more motion in one direction and less direction in another. When oriented in the manner shown in FIG. 7, the rod provides more motion in the flexion and extension directions, and permits less motion in the lateral directions. It does this because the flexible sections of the fastener 20 and rod 30 are substantially aligned along a plane that extends through the fastener and rod axes 107, 203, 205. Therefore, both the fastener 20 and rod 30 are arranged to permit more motion in flexion and extension and less motion in the lateral direction. By orienting the flexible fastener and rod as shown, so that the rod 30 and fastener 20 are aligned to contribute more to the flexion and extension movement and less to the lateral movement, the maximum range of stress distribution and maximum range of motion can be achieved.

Here, both the fastener 20 and the spinal rod 30 include C-shaped flexible sections. Because the fastener and the spinal rod have matching dynamic capabilities, including a similar shaped motion-generating portion, and both using a bumper, the load-sharing benefits obtained by cooperating dynamic fasteners and dynamic rods can be maximized. In such embodiments that use bumpers, the fastener and rod may use bumpers formed of the same material. It is worth noting however, that the bumper materials can vary between components.

Figure 8:
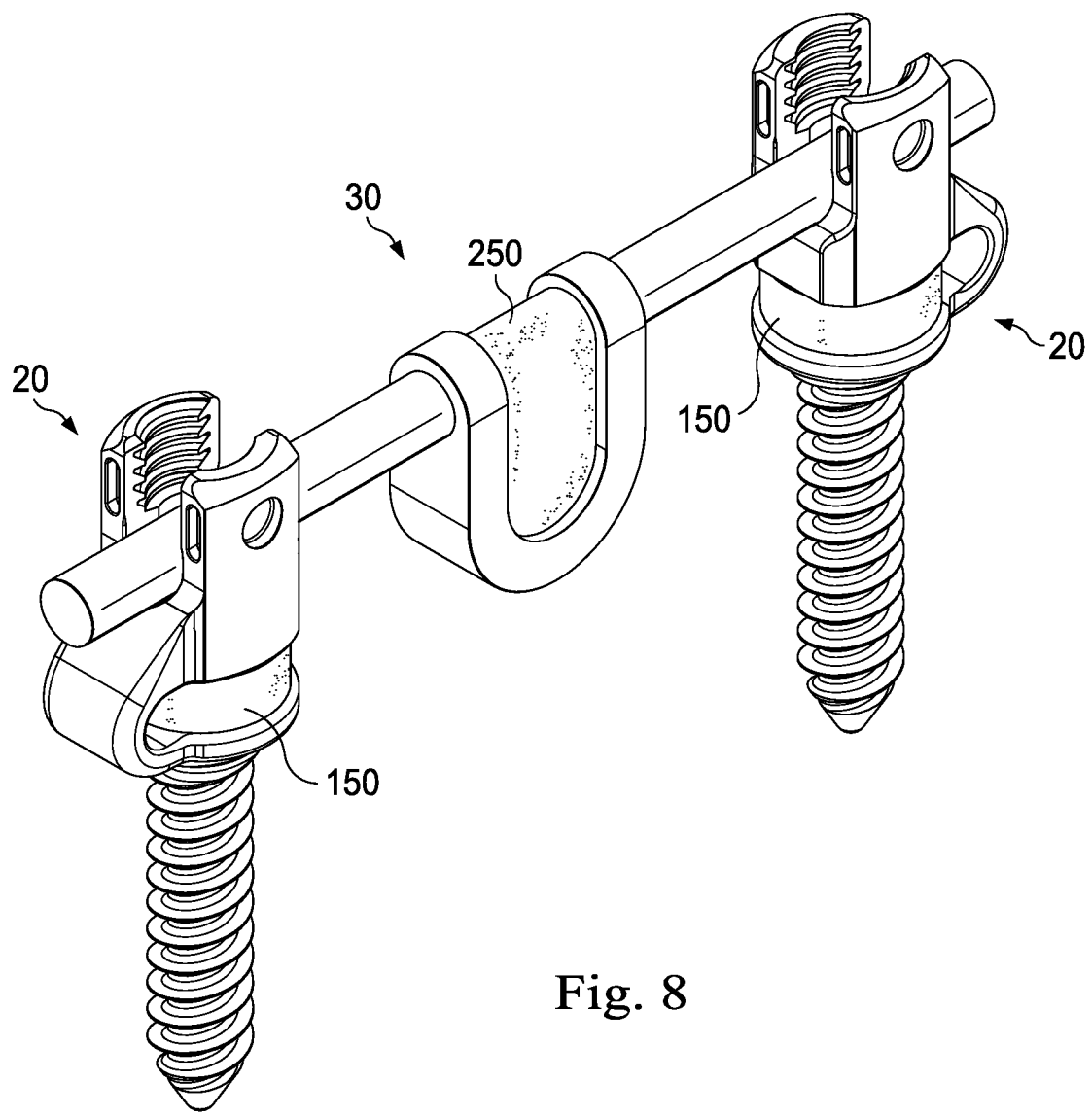
FIG. 8 is an illustration of an exemplary spinal construct including a two dynamic bone fasteners and a dynamic spinal rod for single level spinal stabilization in accordance with one or more aspects of the present disclosure.

FIG. 8 shows another embodiment of an exemplary spinal rod construct 10. This embodiment includes two dynamic screws 20 and the dynamic spinal rod 30. Because the construct 10 comprises three cooperating dynamic constructs, some of the load sharing advantages can be further capitalized. For example, because three dynamic constructs are used, there is an increased distribution of stress and strain under both flexion and extension. In addition, the construct 10 may provide a range of motion greater than the range of motion of the construct in FIG. 7. As described above, the orientation of the rod and fasteners is arranged to compensate for each other to maximize the range of motion. That is, each is arranged to provide a maximum ROM along the same plane.

Figure 9:
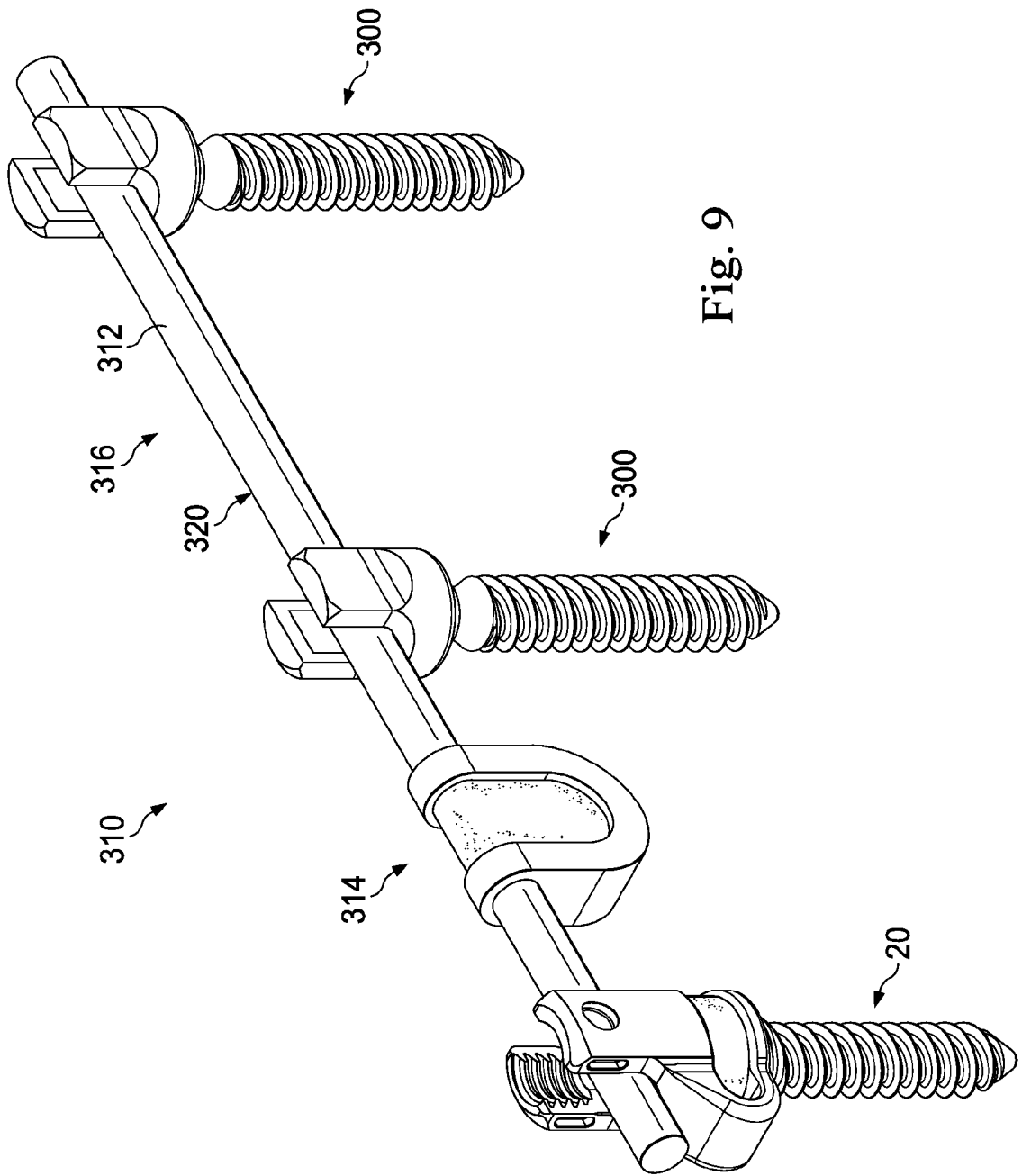
FIG. 9 is an illustration of an exemplary spinal construct including a dynamic bone fastener and a dynamic spinal rod for two-level spinal stabilization with a dynamic level and a fusion level in accordance with one or more aspects of the present disclosure.

FIG. 9 shows another embodiment of an exemplary spinal rod construct, referred to by the reference numeral 310. This embodiment is two level construct meaning it spans and provides support to two levels of the vertebral column. It includes a dynamic screw 20, two multi-axial screws 300, and a partially dynamic spinal rod 320. Here, the spinal rod 320 includes the dynamic spinal rod features described above as in FIG. 7, but includes an extended rigid portion 312 configured for spanning a second vertebral level and for connecting to two conventional multiaxial screws 300. Accordingly, the spinal rod construct 310 includes both a dynamic level 314 and a fusion level 316. Therefore, all the advantages discussed above can be obtained at the dynamic level of the vertebral column, while still providing the opportunity to fuse a different level of the vertebral column.

Figure 10:
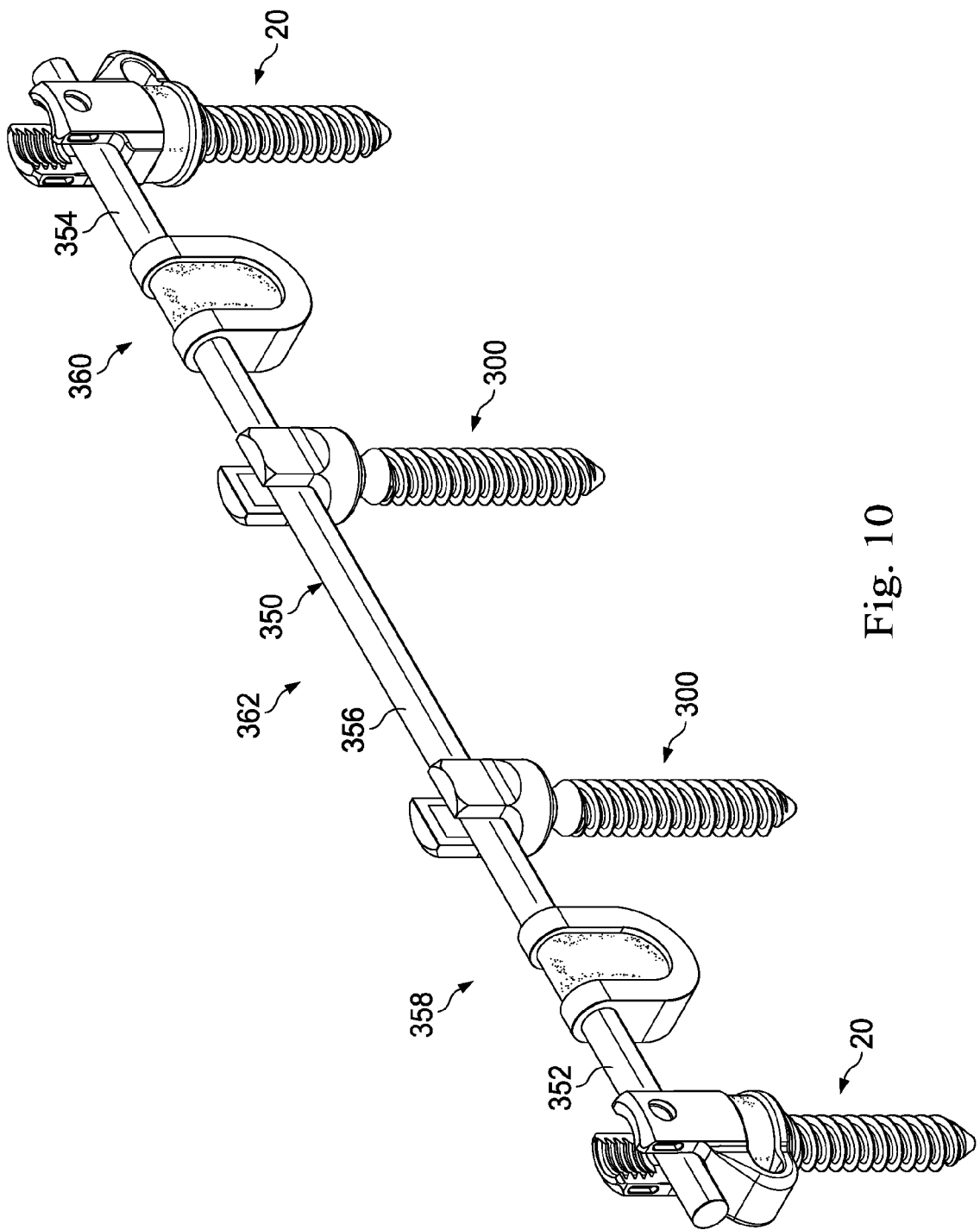
FIG. 10 is an illustration of an exemplary spinal construct including dynamic bone fasteners and a dynamic spinal rod for three-level spinal stabilization with two dynamic levels and a fusion level in accordance with one or more aspects of the present disclosure.

FIG. 10 shows another embodiment of an exemplary spinal rod construct, referred to by the reference numeral 340. This embodiment is a three level construct meaning it spans and provides support to three levels of the vertebral column. It includes two dynamic screws 20, two multi-axial screws 300, and a partially dynamic spinal rod 350. Here, the spinal rod 350 includes two ends 352, 354 having the dynamic spinal rod features described above as in FIG. 7. It also includes an extended rigid portion 356 between the two ends 352, 354. Accordingly, the construct 350 includes a first dynamic level 358, an intermediate fusion level 362, and a second dynamic level 360. Therefore, all the advantages discussed above can be obtained at the dynamic level of the vertebral column, while still providing the opportunity to fuse a different level of the vertebral column. These are just examples and it should be apparent that any number of levels and fusion or dynamic arrangements may be used.

Figure 11:
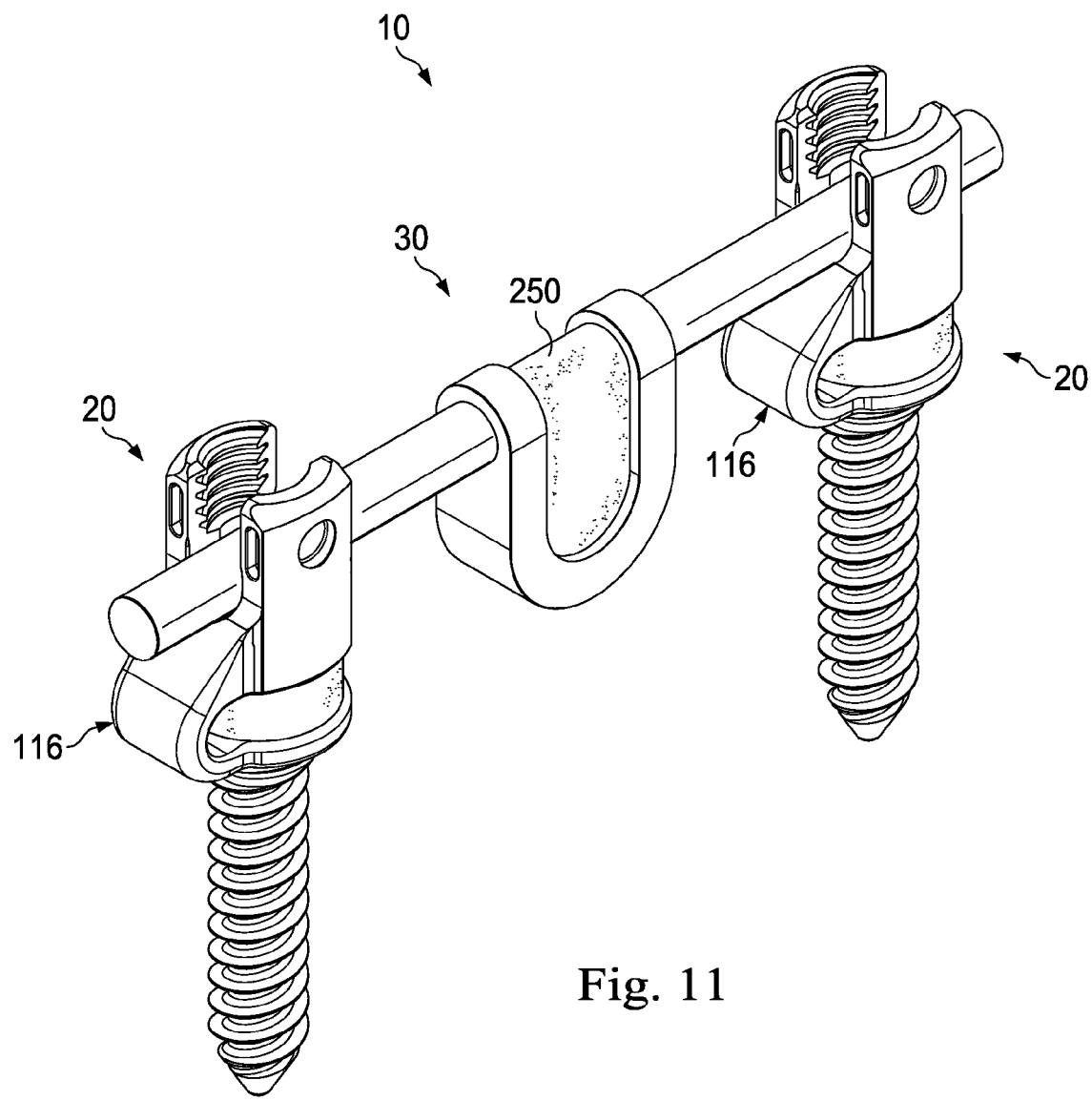
FIG. 11 is an illustration of an exemplary spinal construct including two dynamic bone fasteners and a dynamic spinal rod for single level spinal stabilization where the bone fasteners are oriented in the same direction in accordance with one or more aspects of the present disclosure.

FIG. 11 discloses another example of the rod construct 10 arranged differently than the rod construct in FIG. 8. This embodiment includes two dynamic screws 20 and the dynamic spinal rod 30. However, the orientation of the fasteners 20 is arranged to provide particular advantages to the construct that may not be obtained otherwise. For example, in this instance, the fasteners 20 are arranged so that the connecting portions 116 face the same direction, but the flexible connecting portions 116 are still maintained within substantially the same plane. This may provide particular motion by having the fasteners cooperate to achieve the desired ROM. For example, since the fasteners are arranged to face the same direction, the construct 10 may provide increased motion in one of extension or flexion, and less motion in the other of extension or flexion. The screws may be arranged in any desired orientation to achieve a particular result.

The components of the construct 10 are fabricated from materials suitable for medical applications, including metals, polymers, ceramics, biocompatible materials and/or their composites, depending on the particular application and/or preference of a medical practitioner. For example, the bone fastener 20 and/or the rod 30 can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO4 composites, ceramics and composites thereof such as calcium phosphate (e.g. SKEL-ITE™ manufactured by Biologix Inc.), rigid polymers including polyphenylene, polyamide, polyimide, polyetherimide, polyethylene, polyurethanes of any durometer, epoxy and silicone. Different components may have alternative material composites to achieve various desired characteristics such as strength, rigidity, elasticity, compliance, biomechanical performance, durability and radiolucency or imaging preference. The components may also be fabricated from a heterogeneous material such as a combination of two or more of the above-described materials.

In some examples, the bone fastener 20 and the spinal rod 30 are each formed of two or more materials. In one embodiment, different sections of portions the bone fastener 100 are be fabricated from carbon-reinforced PEEK and an intermediate section can be fabricated from PEEK. In one embodiment, the first and second sections are fabricated from PEEK and the intermediate section is fabricated from carbon-reinforced PEEK. In one embodiment, the fixation portion is fabricated from a first material, such as those described above, and the flexible portion is fabricated from a second material such as, for example, Nitinol, PEEK, carbon-PEEK, a titanium alloy and/or a cobalt-chrome alloy. In one embodiment, alternate materials may be employed in a radial direction of bone fastener 20 and the spinal rod 30 such that stiff materials such as metals or other composites are used in a core of the fastener sections and an outer sheet of lower modulus polymeric material is used in the outer radial portion of the fastener portions, or vice versa.

As a further example, a resistance member, discussed below, of bone fastener 20 and the spinal rod 30 may be fabricated from materials such as silicone, polyurethane, silicone-polyurethane copolymers, polymeric rubbers, polyolefin rubbers, hydrogels, semi-rigid and rigid materials, and biocompatible materials such as elastomers, rubbers, thermoplastic elastomers, thermoset elastomers, elastomeric composites and plastics. It is envisioned that the components of the spinal rod construct can be manufactured via various methods. For example, bone fastener 20 and the spinal rod 30 can be manufactured and assembled via injection-molding, insert-molding, overmolding, compression molding, transfer molding, co-extrusion, pultrusion, dip-coating, spray-coating, powder-coating, porous-coating, machining, milling from a solid stock material, and their combinations. One skilled in the art, however, will realize that such materials and fabrication methods suitable for assembly and manufacture, in accordance with the present disclosure, would be appropriate.

The bone fastener 20 may be employed as a bone screw, pedicle screw or multi-axial screw (MAS) used in spinal surgery. It is contemplated that bone fastener 30 may be coated with an osteoconductive material such as hydroxyapatite and/or osteoinductive agent such as a bone morphogenic protein for enhanced bony fixation to facilitate motion of the treated spinal area. The bone fastener 20, the rod 30 and the bumpers 150, 250 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires can be used, such as being disposed at the end portions of rod 30 and/or along the length thereof adjacent the joint portion 46 or with bumper 150.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

What is claimed is:

1. A spinal construct for implantation in a patient to provide stabilization to a spinal structure with improved load sharing, comprising:
   a flexible spinal rod having a first end and a second end, the flexible spinal rod comprising a C-shaped flexible portion, the spinal rod being configured to provide stabilization to the spinal structure;
   a first bone fastener configured to securely attach to the flexible spinal rod; and
   a second bone fastener configured to securely attach to the flexible spinal rod, the second bone fastener is a dynamic fastener arranged to provide motion in one direction more than another direction, the second bone fastener is monolithic and extends along a longitudinal axis between a proximal portion comprising a pair of spaced apart arms defining a cavity configured to receive the flexible spinal rod and a distal portion configured to penetrate tissue, the second bone fastener includes a C-shaped flexible portion positioned between the proximal and distal portions such that the proximal and distal portions are aligned with the longitudinal axis and the C-shaped flexible portion includes a joint portion positioned offset from the longitudinal axis, the flexible spinal rod and the second bone fastener are oriented to cooperate in a manner that achieves load sharing by dynamically flexing under applied loads in a manner that distributes stresses and strains between the flexible spinal rod and the second bone fastener.

2. The spinal construct of claim 1, wherein the first bone fastener comprises a dynamic fastener arranged to provide motion in one direction more than another direction, the flexible spinal rod, the first bone fastener, and the second bone fastener being oriented to cooperate in a manner that achieves load sharing by dynamically flexing under applied loads in a manner that distributes stresses and strains between the flexible spinal rod and both the first and the second bone fasteners.

3. The spinal construct of claim 1, wherein the second bone fastener comprises a flexible bumper configured to dampen movement in at least one of flexion and extension.

4. The spinal construct of claim 3, wherein the flexible spinal rod comprises a flexible bumper configured to dampen movement in at least one of flexion and extension.

5. The spinal construct of claim 1, wherein the second bone fastener is configured to provide more motion in a flexion or extension direction than in a lateral direction, and wherein the flexible spinal rod is configured to provide more motion in a flexion or extension direction than in a lateral direction.

6. The spinal construct of claim 1, wherein the flexible portion of the second bone fastener is an elastically flexible arcuate connecting portion.

7. The spinal construct of claim 6, wherein the first bone fastener comprises a dynamic fastener arranged to provide motion in one direction more than another direction, the flexible spinal rod, the first bone fastener, and the second bone fastener being oriented to cooperate in a manner that achieves load sharing by dynamically flexing under applied loads in a manner that distributes stresses and strains between the flexible spinal rod and both the first and the second bone fasteners, wherein the first bone fastener comprises an elastically flexible arcuate connecting portion, and wherein the first and second bone fasteners are oriented so that the arcuate connecting portions of the first and second bone fasteners are aligned in the same direction.

8. The spinal construct of claim 1, wherein the flexible spinal rod comprises:
   a first portion having a first longitudinal axis, the first portion being connectable to the first bone fastener; a second portion having a second longitudinal axis, the second portion being connectable to the second bone fastener;
   wherein the rod flexible portion extends between and connects the first and second portions of the spinal rod, the rod flexible portion being offset from both the first and the second longitudinal axes.

9. The spinal construct of claim 8, wherein the rod flexible portion comprises an elastically flexible arcuate connecting portion.

10. The spinal construct of claim 1, wherein at least one of the flexible spinal rod and the second bone fastener comprises polyetheretherketone (PEEK) and silicone.

11. The spinal construct of claim 1, wherein the arms are substantially parallel to the longitudinal axis and the C-shaped flexible portion of the second bone fastener includes an inner surface defining a passageway extending perpendicular to the longitudinal axis.

12. The spinal construct of claim 1, wherein the C-shaped flexible portion of the second bone fastener is made from the same material as the proximal and distal portions of the second bone fastener.

13. The spinal construct of claim 1, wherein the C-shaped flexible portion of the second bone fastener defines a cavity having an elastic bumper disposed therein to prevent creep and improve shape recovery, the bumper being monolithically formed with the C-shaped flexible portion of the second bone fastener.

14. A spinal construct for implantation in a patient to provide stabilization to a spinal structure with improved load sharing, comprising:
   a flexible spinal rod having a first end and a second end, the spinal rod being configured to provide stabilization to the spinal structure, the spinal rod being configured in a manner that provides relatively more motion in a flexion and extension direction and relatively less motion in a lateral direction; and
   a first bone fastener configured to securely attach to the flexible spinal rod, the first bone fastener is monolithic and extends along a longitudinal axis between a proximal portion comprising a pair of spaced apart arms defining a cavity configured to receive the spinal rod and a distal portion configured to penetrate tissue, the first bone fastener comprising a C-shaped flexible portion positioned between the proximal and distal portions such that the proximal and distal portions are aligned with the longitudinal axis and the C-shaped flexible portion includes a joint portion positioned offset from the longitudinal axis, the first bone fastener is configured in a manner that provides relatively more motion in a flexion and extension direction and relatively less motion in a lateral direction, the flexible spinal rod and the first bone fastener are oriented to cooperate in a manner that achieves load sharing by dynamically flexing under applied loads in a manner that distributes stresses and strains between the flexible spinal rod and the first bone fastener.

15. The spinal construct of claim 14, wherein the C-shaped flexible portion defines a cavity having an elastic bumper disposed therein to prevent creep and improve shape recovery.

16. The spinal construct of claim 15, wherein the flexible spinal rod includes a C-shaped flexible portion.

17. The spinal construct of claim 14, further comprising a second bone fastener comprising a flexible bumper configured to dampen movement in at least one of flexion and extension.

18. The spinal construct of claim 17, wherein the flexible spinal rod comprises a flexible bumper configured to dampen movement in at least one of flexion and extension.

19. The spinal construct of claim 14, wherein the flexible portion is an elastically flexible arcuate connecting portion.

20. The spinal construct of claim 14, wherein the flexible spinal rod comprises an elastically flexible arcuate connecting portion.

* * * * *